(12) United States Patent
Tsujii

(10) Patent No.: US 9,279,775 B2
(45) Date of Patent: Mar. 8, 2016

(54) X-RAY IMAGING APPARATUS, METHOD OF CONTROLLING THE SAME, AND COMPUTER PROGRAM

(75) Inventor: Osamu Tsujii, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 328 days.

(21) Appl. No.: 13/610,555

(22) Filed: Sep. 11, 2012

(65) Prior Publication Data

US 2013/0003920 A1   Jan. 3, 2013

Related U.S. Application Data

(63) Continuation of application No. 13/082,613, filed on Apr. 8, 2011, now Pat. No. 8,290,118, which is a continuation of application No. 12/881,972, filed on Sep. 14, 2010, now Pat. No. 7,940,888, which is a continuation of application No. PCT/JP2010/001988, filed on Mar. 19, 2010.

(30) Foreign Application Priority Data

Apr. 3, 2009   (JP) .................................. 2009-091480

(51) Int. Cl.
*G01N 23/04*   (2006.01)
*A61B 6/00*   (2006.01)

(52) U.S. Cl.
CPC ............ *G01N 23/046* (2013.01); *A61B 6/4007* (2013.01); *A61B 6/4028* (2013.01); *A61B6/4441* (2013.01); *A61B 6/587* (2013.01); *A61B 6/589* (2013.01); *G01N 23/04* (2013.01); *A61B 6/4021* (2013.01)

(58) Field of Classification Search
CPC ........ A61B 6/024; A61B 6/0306; A61B 6/02; A61B 6/4441; A61B 6/4007; A61B 6/4021; A61B 6/4028; A61B 6/587; A61B 6/589; A61B 6/032; A61B 6/4085; A61B 6/4233; A61B 6/5241; A61B 6/547; A61B 5/1135; A61B 6/027; A61B 6/03; A61B 6/4014; A61B 6/466; A61B 6/486; G01N 23/046
USPC ................. 378/4, 9, 21–27, 62, 92, 98.8, 121
See application file for complete search history.

(56) References Cited

U.S. PATENT DOCUMENTS

| | | | |
|---|---|---|---|
| 4,099,880 A | 7/1978 | Kano | |
| 6,222,904 B1 | 4/2001 | Berestov | |
| 8,290,118 B2 * | 10/2012 | Tsujii | ............................... 378/21 |
| 2009/0022264 A1 * | 1/2009 | Zhou et al. | ......................... 378/5 |

FOREIGN PATENT DOCUMENTS

| | | |
|---|---|---|
| CN | 1126578 A | 7/1996 |
| CN | 101395691 A | 3/2009 |
| JP | 0549632 A | 3/1993 |
| JP | 2000166909 A | 6/2000 |
| JP | 2001286458 A | 10/2001 |
| JP | 2005261838 A | 9/2005 |

* cited by examiner

*Primary Examiner* — Irakli Kiknadze
(74) *Attorney, Agent, or Firm* — Canon USA Inc. IP Division

(57) ABSTRACT

An X-ray imaging apparatus includes an X-ray source including a plurality of X-ray focuses, an X-ray detector which detects X-rays emitted from the X-ray focuses and transmitted through an object, and a control unit which controls the X-ray source and the X-ray detector. The X-ray imaging apparatus selects a pair of X-ray focuses, of X-ray focuses of the plurality of X-ray focuses which project images on the X-ray detector through a region of interest which is an imaging region of the object, from which emitted X-rays define an intersecting angle coinciding with a predetermined angle in the region of interest, and decides an X-ray focus to be used for imaging from X-ray focuses between the selected pair of X-ray focuses. An X-ray image is captured by emitting X-rays from the decided X-ray focus and causing the X-ray detector to detect the X-rays.

15 Claims, 7 Drawing Sheets

X-RAY IMAGING APPARATUS, METHOD OF CONTROLLING THE SAME, AND COMPUTER PROGRAM

CROSS-REFERENCE TO RELATED APPLICATIONS

This application is a CONTINUATION of co-pending U.S. patent application Ser. No. 13/082,613 filed 8 Apr. 2011, which is a CONTINUATION of prior U.S. patent application Ser. No. 12/881,972 filed 14 Sep. 2010, now U.S. Pat. No. 7,940,888 issued 10 May 2011, which is a CONTINUATION of International application No. PCT/JP2010/001988 filed 19 Mar. 2010, which claims priority from Japanese Patent Application No. 2009-091480 filed 3 Apr. 2009. The disclosures of the above-referenced applications and patent are hereby incorporated by reference herein in their entirety.

TECHNICAL FIELD

The present invention relates to an X-ray imaging apparatus, a method of controlling the same, and a computer program for the above.

BACKGROUND ART

A tomography apparatus controls the motion range of an X-ray apparatus or two-dimensional detector in accordance with an imaging region. Japanese Patent Application Laid-Open No. 2004-041702 (PLT1) and International Patent Application Publication WO/2007/100105 (PLT2) are related to such a tomography apparatus. PLT1 discloses a radiographic apparatus that radiographs an object with radiation from a movable radiation source. The radiographic apparatus detects a radiographic image of an object supported by a support portion by using a detection unit. At this time, based on the information of the position of the radiation source and an imaging target region of an object, a control unit controls the movement of at least one of the detection unit and the support portion so as to detect a projection image of the imaging target region.

A tomography apparatus designed to radiograph an object with radiation from a radiation source controls each of the electron sources of the radiation source, which are distributed two-dimensionally, to generate multi X-ray beams, and detects a radiographic image of the object by using a detector (see PLT2). Using such multi X-ray beams can perform tomography without moving both the radiation source and the detector.

CITATION LIST

Patent Literature

PLT1: Japanese Patent Application Laid-Open No. 2004-041702

PLT2: International Patent Application Publication WO/2007/100105

In tomography, however, it is impossible to maintain the resolution in the Z-axis (thickness) direction unless imaging is performed at a predetermined tomographic angle or more. There has been provided no technique capable of performing tomography in a limited space such as an operating room while maintaining a predetermined tomographic angle or more. There has been proposed no effective technique of selecting a plurality of X-ray sources when performing tomography at a predetermined tomographic angle or more.

The present invention provides a technique capable of performing tomography while maintaining a predetermined tomographic angle or more without simultaneously moving an X-ray apparatus and a two-dimensional detector at the time of imaging.

SUMMARY OF INVENTION

In order to solve the above problem, according to the present invention, there is provided an X-ray imaging apparatus including an X-ray source including a plurality of X-ray focuses, an X-ray detector which detects X-rays emitted from the X-ray focuses and transmitted through an object, and control means for controlling the X-ray source and the X-ray detector, the apparatus comprising, selection means for selecting a pair of X-ray focuses, of X-ray focuses of the plurality of X-ray focuses which are configured to project images on the X-ray detector through a region of interest which is an imaging region of the object, from which emitted X-rays define an intersecting angle coinciding with a predetermined angle in the region of interest, and decision means for deciding an X-ray focus to be used for imaging from X-ray focuses between the pair of X-ray focuses selected by the selection means, wherein the control means captures an X-ray image by causing emission of X-rays from the X-ray focus decided by the decision means and causing the X-ray detector to detect the X-rays.

The present invention can provide a technique capable of performing tomography while maintaining a predetermined tomographic angle or more without simultaneously moving an X-ray apparatus and a two-dimensional detector at the time of imaging.

Other features and advantages of the present invention will be apparent from the following description taken in conjunction with the accompanying drawings, in which like reference characters designate the same or similar parts throughout the figures thereof.

BRIEF DESCRIPTION OF DRAWINGS

The accompanying drawings, which are incorporated in and constitute a part of the specification, illustrate embodiments of the invention and, together with the description, serve to explain the principles of the invention.

DESCRIPTION OF EMBODIMENTS

Figure 1:
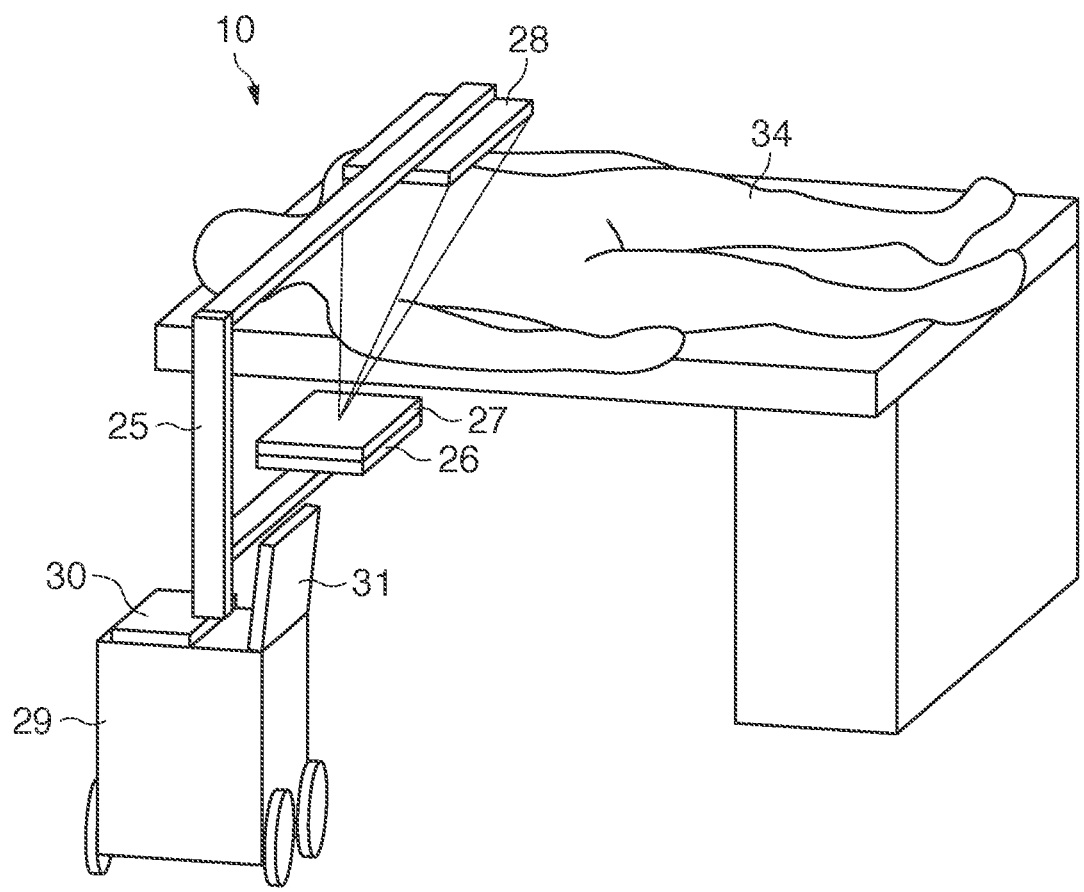
FIG. 1 is a perspective view showing an example of the arrangement of an X-ray imaging system according to an embodiment of the present invention.

A preferred embodiment of the present invention will be described in detail with reference to the accompanying drawings. FIG. 1 shows a case in which an X-ray imaging system 10 according to the embodiment of the present invention is capturing an X-ray tomogram of a human body. A two-dimensional X-ray detector 28 and a multi X-ray source 26 are fixed to a C-ram 25. A stop unit 27 is fixed on the emission side of the multi X-ray source 26. The multi X-ray source 26 is placed on the backside of a patient. The multi X-ray source 26 includes N×M X-ray focuses which are arranged two-dimensionally. The X-rays emitted from a transmission target of the multi X-ray source 26 are transmitted through a human body 34 as an object and reach the two-dimensional X-ray detector 28. The two-dimensional X-ray detector 28 outputs the intensity distribution of the incident X-rays, calculates an X-ray tomogram, and displays it on a display unit 31. A control panel 30 is connected to a control unit 29. The control unit 29 decides a region of interest (to be described later) and an imaging mode for tomography (a maximum tomographic angle mode or fixed tomographic angle mode) in accordance with the operation by a doctor via the control panel 30. In addition, a tomogram is calculated based on the image read from the two-dimensional X-ray detector 28 and is displayed on the display unit 31.

Figure 2:
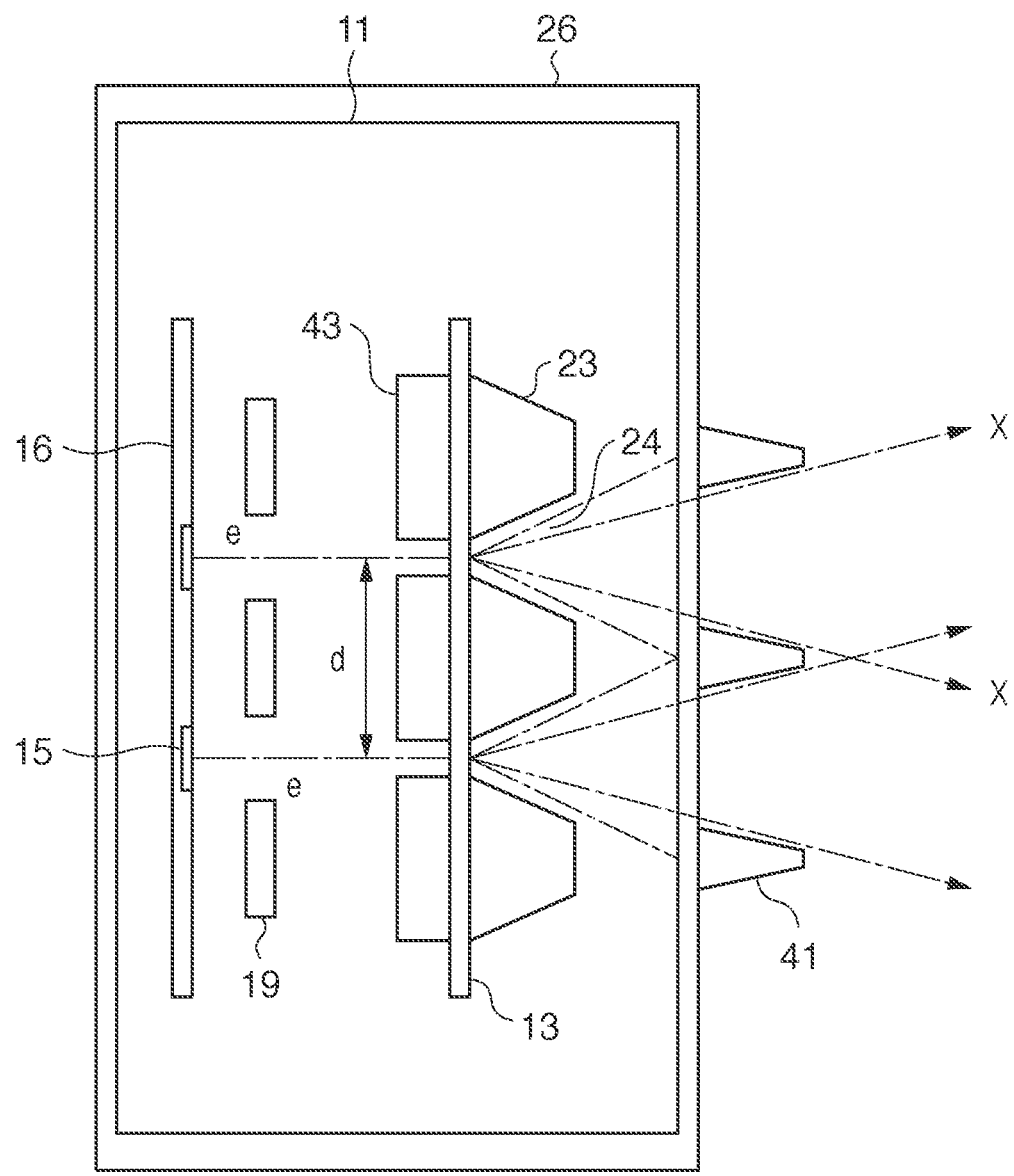
FIG. 2 is a view for explaining the structure of a multi X-ray source 26 according to the embodiment of the present invention.

The structure of the multi X-ray source 26 will be described next with reference to FIG. 2. The multi X-ray source 26 includes an element array 16. Each of multi electron emission elements 15 arranged on the element array 16 emits electrons. Emitted electrons are shaped by a lens electrode 19 and accelerated by an accelerating electric field to collide with a transmission target 13. An in-vacuum X-ray shield 23 limits the direction of the X-rays generated by the transmission target 13. It is possible to further limit the direction of the X-rays by using an in-atmosphere X-ray shield 41. Note however that this embodiment uses the stop unit 27 in place of the in-atmosphere X-ray shield 41. An arrangement using the stop unit 27 will be described later with reference to FIGS. 6 and 7.

A method of deciding a region of interest in this embodiment will be described next. A region of interest is a region which corresponds to an imaging region of the object 34 from which an X-ray tomogram is to be captured, and through which X-rays emerging from a plurality of X-ray focuses of the multi X-ray source 26 are commonly transmitted. It is possible to decide a region of interest by the following three types of methods. The first method is a method of making the operator set the apparatus by eye measure to match with specified values set in advance by the control unit 29 including a computer. In this case, the specified values include the distance from the two-dimensional X-ray detector 28 to a region of interest, the distance from the multi X-ray source 26 to the region of interest, and the size of the region of interest. The second method is a method of making the operator input visually measured values to the control unit 29 after setting the apparatus for a patient. The third method is a decision method using X-ray images. A merit of the third method is that it involves few errors.

Figure 3:
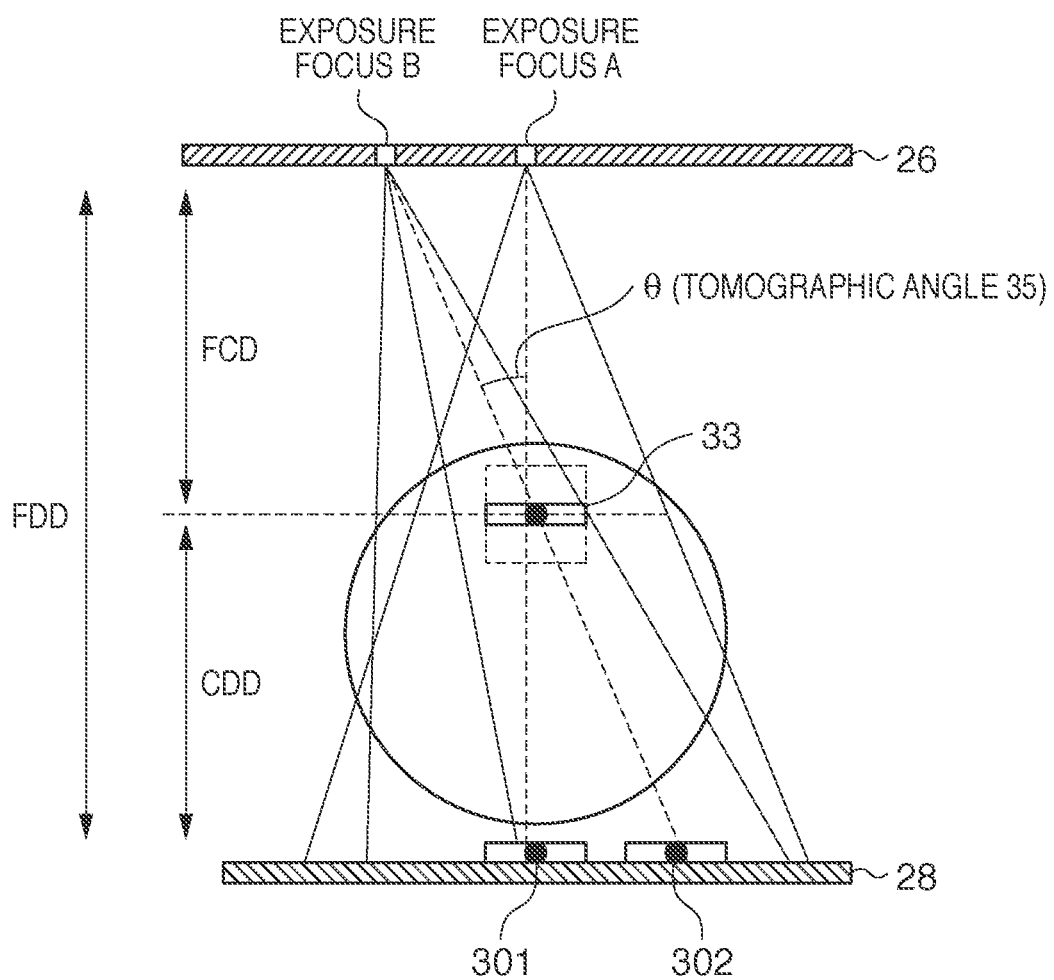
FIG. 3 is a view for explaining a method of deciding a region of interest according to the embodiment of the present invention.

A method of deciding a region of interest in the third method will be described next with reference to FIG. 3. The items which should be decided regarding a region of interest 33 include the distance from the two-dimensional X-ray detector 28 to the region of interest 33, the distance from the multi X-ray source 26 to the region of interest 33, and the size of the region of interest 33. The size of the region of interest 33 may be expressed in terms of a sphere or rectangular parallelepiped. In this case, for the sake of convenience, the size is expressed in terms of a rectangular parallelepiped, and the distances from the two-dimensional X-ray detector 28 and the multi X-ray source 26 to the region of interest 33 are those to the center of a cube as an end point. This apparatus captures X-ray images from an exposure focus A and an exposure focus B before tomography. The operator can designate points of interest (analytical portions of interest indicated by the bullets) 301 and 302 on the two X-ray images obtained from the X-rays from the respective exposure focuses. Referring to FIG. 3, an intersecting angle θ between a line segment connecting the exposure focus A and the point of interest 301 and a line segment connecting the exposure focus B and the point of interest 302 will be referred to as a tomographic angle 35.

An X-ray image is output to the display unit 31. Since the X-ray image corresponds to the detection surface of the two-dimensional X-ray detector 28, connecting the exposure focuses A and B to the points of interest 301 and 302 with straight lines can obtain the center of the region of interest 33. Assume that the distance (FDD: Focus Detector Distance) from the center of the multi X-ray source 26 to the two-dimensional X-ray detector 28 is known. In addition, the distances between the exposure focus A and the exposure focus B and the distance between the point of interest 301 and the point of interest 302 are also known. It is possible to obtain the distance (CDD: Center Detector Distance) from the two-dimensional X-ray detector 28 to the region of interest 33 and the distance (FCD: Focus Center Distance) from the multi X-ray source 26 to the region of interest 33 based on these ratios. The operator can designate the size of the region of interest 33 with a mouse or the like. In this embodiment, the region of interest 33 is assumed to be a cube. Therefore, the operator can designate the size of the region of interest 33 (one side of the cube: P) even by designation on an X-ray image plane.

In addition, it is possible to automatically decide the region of interest 33 by image processing. During a surgical operation, it is possible to place a radiopaque object (bead) in the actual region of interest 33. It is therefore only required to search for a radiopaque object by image processing. If it is impossible to place a radiopaque object, a high-contrast lesion or medical treatment component can be set as a target for a point of interest. According to the above description, two X-ray images are used. However, it is possible to use three or more X-ray images to improve the accuracy.

Figure 4:
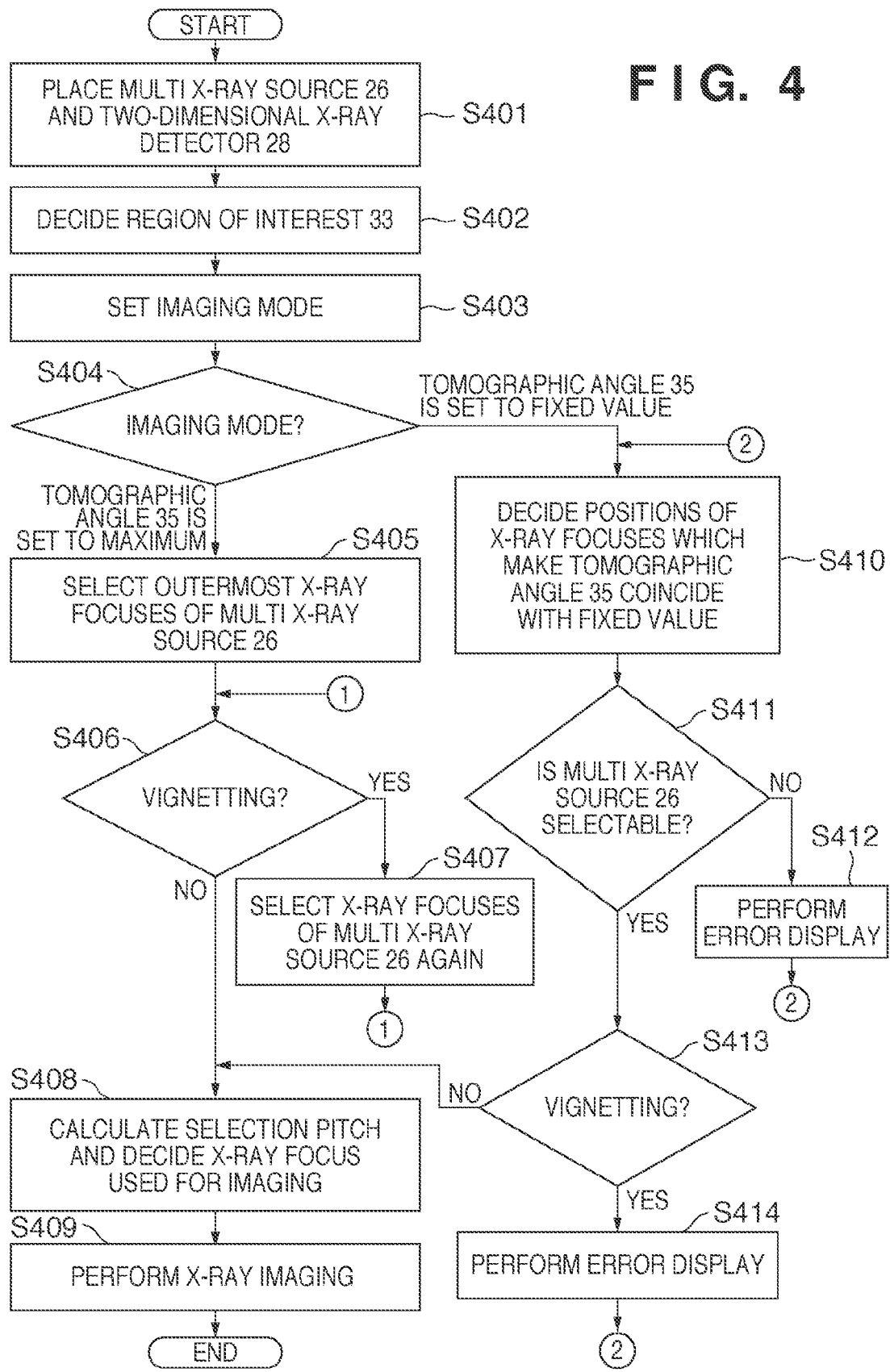
FIG. 4 is a flowchart for X-ray focus selection processing according to the embodiment of the present invention.

A method of selecting X-ray focuses to be used for imaging from a plurality of X-ray focuses will be described next with reference to the flowchart of FIG. 4 and the schematic view of FIG. 5. First of all, in step S401, the operator sets the X-ray imaging system 10 shown in FIG. 1 for the object (patient) 34. In step S402, the region of interest 33 is decided by performing X-ray irradiation in the above manner. Note however that methods of deciding the region of interest 33 include a method without the above X-ray irradiation. In step S403, this system sets an imaging mode based on input operation by the operator. This embodiment includes two imaging modes. One is a mode of imaging upon setting the tomographic angle 35 to the maximum in tomography. The other is a mode of imaging upon setting the tomographic angle 35 to a predetermined angle as a fixed value (preset value). The tomographic angle 35 influences the resolution of a tomogram in the Z direction (the thickness direction of the region of interest 33 or the direction from the multi X-ray source 26 to the detector 28).

In step S404, the system determines the set mode. If the mode of setting the tomographic angle 35 to the maximum is set, the process shifts to step S405. If the mode of setting the tomographic angle 35 to a predetermined angle as a fixed value, the process shifts to step S408.

The mode of imaging upon setting the tomographic angle 35 to the maximum in steps S405 to S408 will be described first. In the mode of imaging upon setting the tomographic angle 35 to the maximum, the system selects, in step S405, outermost X-ray focuses of the multi X-ray source 26 which maximize the tomographic angle 35. In step S406, when X-rays emerge from the selected X-ray focuses so as to intersect each other at the center of the region of interest 33, the system determines whether transmitted X-rays fall outside the two-dimensional X-ray detector 28 (vignetting occurs). In this determination, the system uses the ratio between a distance CDD from the two-dimensional X-ray detector 28 to the region of interest 33 and a distance FCD from the multi X-ray source 26 to the region of interest 33. That is, the system obtains an X-ray irradiation region of the two-dimensional X-ray detector 28 by using the length between X-ray focuses and the ratio when the tomographic angle 35 is set to the maximum. If the irradiation region is larger than the detection surface of the two-dimensional X-ray detector 28, the system can determine that vignetting will occur. If no vignetting will occur (NO in step S406), the system decides to select specific X-ray focuses inside the outermost X-ray focuses based on the selected pitch in step S408. 5a in FIG. 5 indicates a case in which transmitted X-rays do not fall outside the detection surface of the two-dimensional X-ray detector 28. If vignetting will occur (YES in step S406), the system selects X-ray focuses, of the X-ray focuses of the multi X-ray source 26, which are located more inwardly again in step S407. The process then returns to step S406 to continue the processing. 5b in FIG. 5 indicates a case in which when transmitted X-rays fall outside the two-dimensional X-ray detector 28, the outermost X-ray focuses are limited to prevent the transmitted X-rays from slipping from detection.

In this embodiment, the system repeats the processing from step S405 to step S407, and selects a pair of X-ray focuses, of the X-ray focuses which allow to project images on the two-dimensional X-ray detector 28 through a region of interest without causing vignetting, which are located outermost of the multi X-ray source. This makes it possible to specify a pair of X-ray focuses from which X-rays transmitted through the region of interest 33 decided in step S402 can be emitted and which can maximize the tomographic angle 35.

The processing in step S408 will be described below. In tomography, the image resolution in the Z-axis direction depends on the tomographic angle 35, and SN(Signal to Noise) depends on the number of frames to be captured. Note however that increasing the number of frames will increase the amount of exposure to the patient. If a number N (N is an integer equal to or more than 2) of frames is set, a selection angle pitch ρ can be expressed by θ/(N−1) based on a tomographic angle θ35 and the number N of frames. It is possible to approximate a selection pitch p of X-ray focuses (intervals at which X-ray focuses are selected) on the multi X-ray source 26 by expression (1) given below using the distance FCD from the multi X-ray source 26 to the region of interest 33.

$$p \approx FCD*\tan(\theta/(N-1)) \quad (1)$$

However, since actual arrangement intervals w of the X-ray sources on the multi X-ray source 26 are physically fixed, p/w is not necessarily an integer. In this embodiment, it is possible to express an X-ray focus to be selected as X(trunc(n*(p/w))+a) by letting n be a natural number (n=1, 2, ...) and dropping the fractional portion of n*(p/w). Note that a represents an offset value for specifying the first X-ray focus to be selected, and takes an integral value. Note that if the selection angle pitch ρ is a fixed value, a selection pitch p1 on the multi X-ray source 26 can be approximated by expression (2) regardless of the tomographic angle θ35.

$$p1 \approx FCD*\tan(\rho) \quad (2)$$

An X-ray focus to be selected at this time is expressed by X(trunc(n*(p1/w))+a). It is important in this case that even if either the number N of frames in tomography or the selection angle pitch ρ is fixed, the X-ray source pitch of the multi X-ray source 26 is decided depending on FCD. If X-ray focuses to be used at the time of X-ray imaging are decided in the above manner, this system captures X-ray images in step S409 by sequentially emitting X-rays from the decided X-ray focuses and making the control unit 29 receive transmitted X-ray images from the two-dimensional X-ray detector 28. In this case, the multi X-ray source 26 can simultaneously emit X-rays from a plurality of X-ray focuses. However, in order to avoid a reduction in contrast due to scattered radiation, the multi X-ray source 26 preferably emits X-rays while sequentially switching X-ray focuses. It is possible to set the switching timing to about 30 msec. When using, for example, 30 X-ray focuses, the system can perform tomography in one sec. When the system is to perform high-speed imaging, the stop unit 27 prepares in advance stop apertures corresponding to a plurality of X-ray focuses selected before the start of imaging.

The mode of imaging upon setting the tomographic angle 35 to the fixed value (preset value) in steps S410 to S414 will be described next. First of all, in step S410, the system calculates X-ray focuses that make the tomographic angle 35 coincide with a predetermined angle. The system performs this calculation by using the position and size of the region of interest 33, the distance FCD from the center of the multi X-ray source 26 to the region of interest 33, the distance CDD from the two-dimensional X-ray detector 28 to the region of interest 33, and the sizes of the multi X-ray source 26 and two-dimensional X-ray detector 28. Assume a geometric system in which a vertical line passing through the center of the two-dimensional X-ray detector 28 passes through the center of the multi X-ray source 26. Assume also that selected X-ray focuses are arranged to be point-symmetric about the centers on the multi X-ray source 26 and two-dimensional X-ray detector 28.

In step S411, the system determines whether the X-ray focuses decided in step S410 can be selected on the multi X-ray source 26. If they can be selected, the process shifts to step S413. If there are no X-ray focuses which can be selected, the process shifts to step S412. For example, as indicated by 5c in FIG. 5, when a region of interest is located near the two-dimensional X-ray detector 28, the positions decided in step S410 may fall outside the multi X-ray source 26. In such a case, the display unit 31 displays an error indicating that the X-ray focuses cannot be set (cannot be selected) in step S412. The display unit 31 also displays the current values of the distances FCD and CDD and the desired values of the respective distances for allowing the X-ray focuses to be selected. This allows the operator to adjust the positional relationship between the multi X-ray source 26 and the two-dimensional X-ray detector 28 by referring to the desired values displayed on the display unit 31. The process therefore returns to step S410 to perform processing in the positional relationship between the multi X-ray source 26 and the two-dimensional X-ray detector 28 after adjustment corresponding to the error display in step S412. Note that it is possible to perform position adjustment automatically instead of manually.

A case in which the system determines in step S411 that the X-ray focuses can be selected will be described next. In this case, the process shifts to step S413 to determine whether transmitted X-rays from the selected X-ray focuses fall outside the two-dimensional X-ray detector 28 (vignetting occurs). The determination method in this case is the same as that in step S406. As indicated by 5d in FIG. 5, for example, if no vignetting occurs (NO in step S413), the process shifts to step S408. In step S408, the system calculates a selection pitch according to expressions (1) and (2) as described above, and selects X-ray focuses to be used for tomography. In contrast, as indicated by 5e in FIG. 5, if vignetting occurs (YES in step S413), the process shifts to step S414. In step S414, the display unit 31 displays the current values of the distances FCD and CDD and desired values for the prevention of vignetting at the same time when performing error display. This allows the operator to adjust the positional relationship between the multi X-ray source 26 and the two-dimensional X-ray detector 28 by referring to the desired values displayed on the display unit 31 as in the case of step S412. The process returns to step S410 to perform processing in the positional relationship between the multi X-ray source 26 and the two-dimensional X-ray detector 28 after adjustment corresponding to the error display in step S414. Note that it is possible to perform position adjustment automatically instead of manually.

Figure 5:
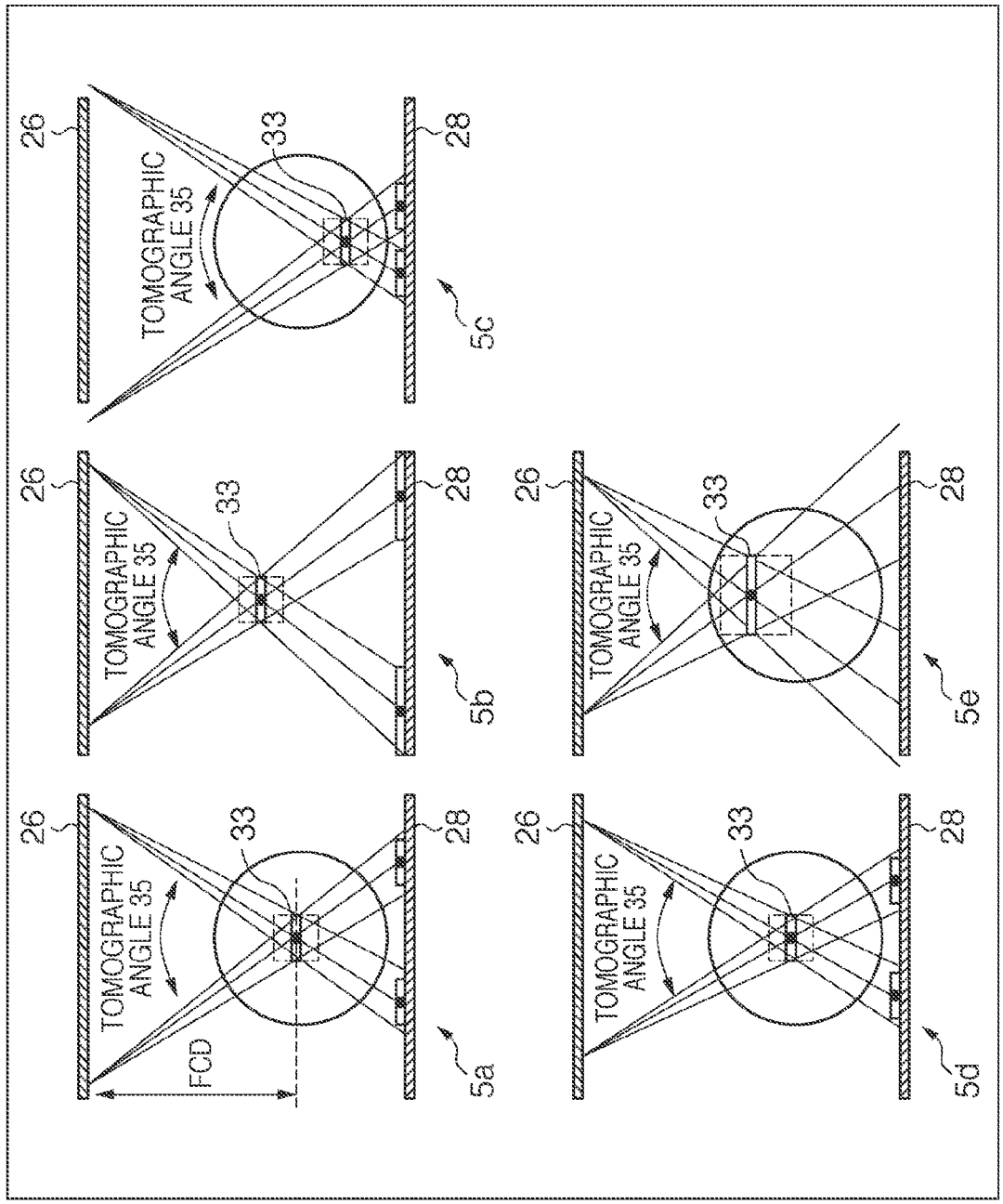
FIG. 5 is a view for explaining a method of selecting X-ray focuses according to the embodiment of the present invention.

Although the above case has been described in the one-dimensional method with reference to FIG. 5 for the sake of convenience, it is possible to extend the method executed in a one-dimensional manner to a two-dimensional method. The above description is the case in which the system performs error display in step S412 or S414 to allow the operator to manually adjust the positional relationship between the multi X-ray source 26 and the two-dimensional X-ray detector 28 or to automatically adjust the positional relationship. However, the embodiment of the present invention is not limited to the adjustment of the positional relationship. For example, it is possible to change the fixed value of the tomographic angle 35. More specifically, the value of the tomographic angle 35 may be decreased by a predetermined value. In this case, if the system determines in step S411 that the X-ray focuses cannot be selected or determines in step S413 that vignetting occurs, the system sequentially decreases the value of the tomographic angle 35 a predetermined value at a time to narrow down the value to a value that allows the X-ray focuses to be selected and prevents the occurrence of vignetting.

Figure 6:
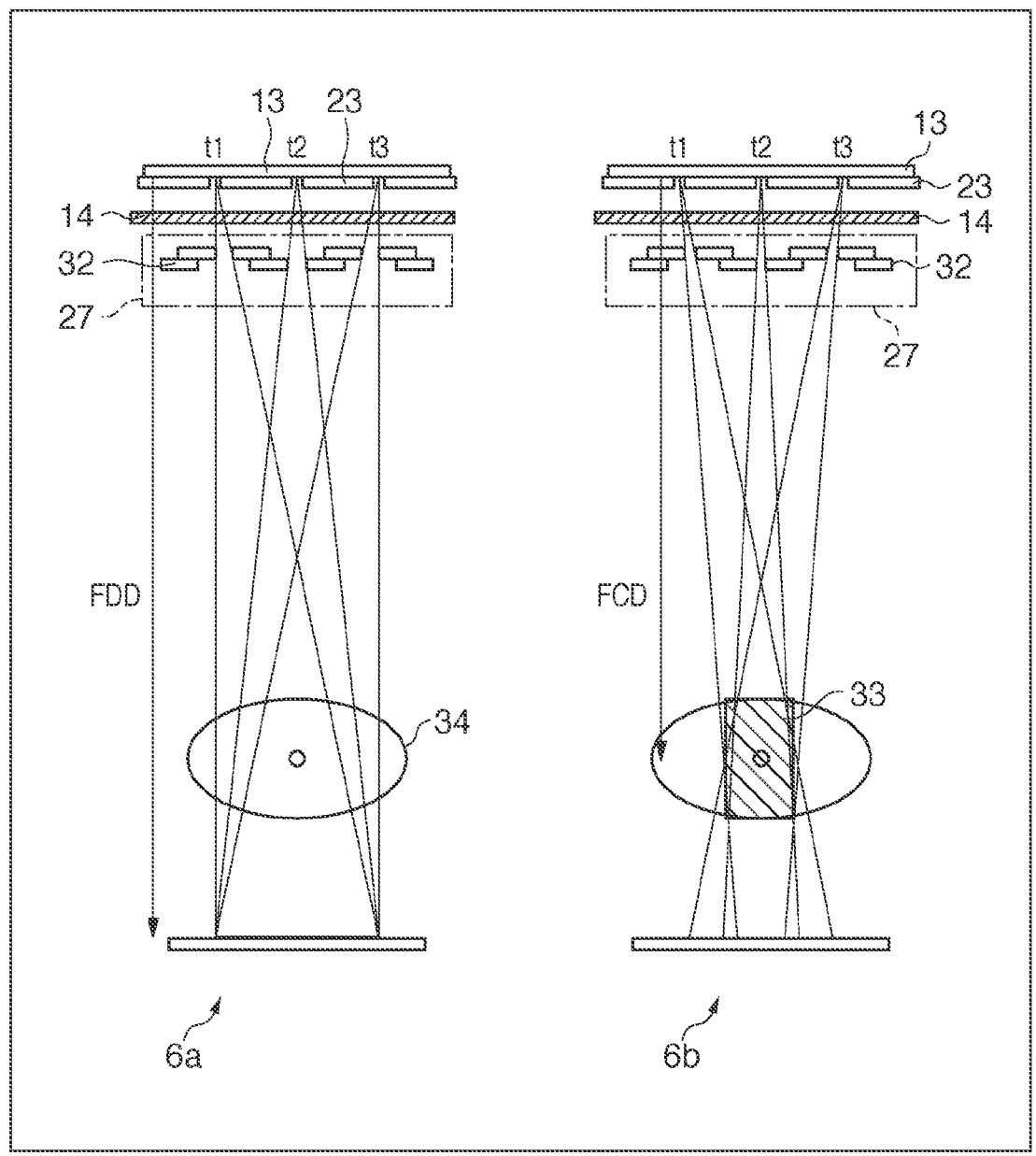
FIG. 6 is a side view of a stop unit according to the embodiment of the present invention.
Figure 7:
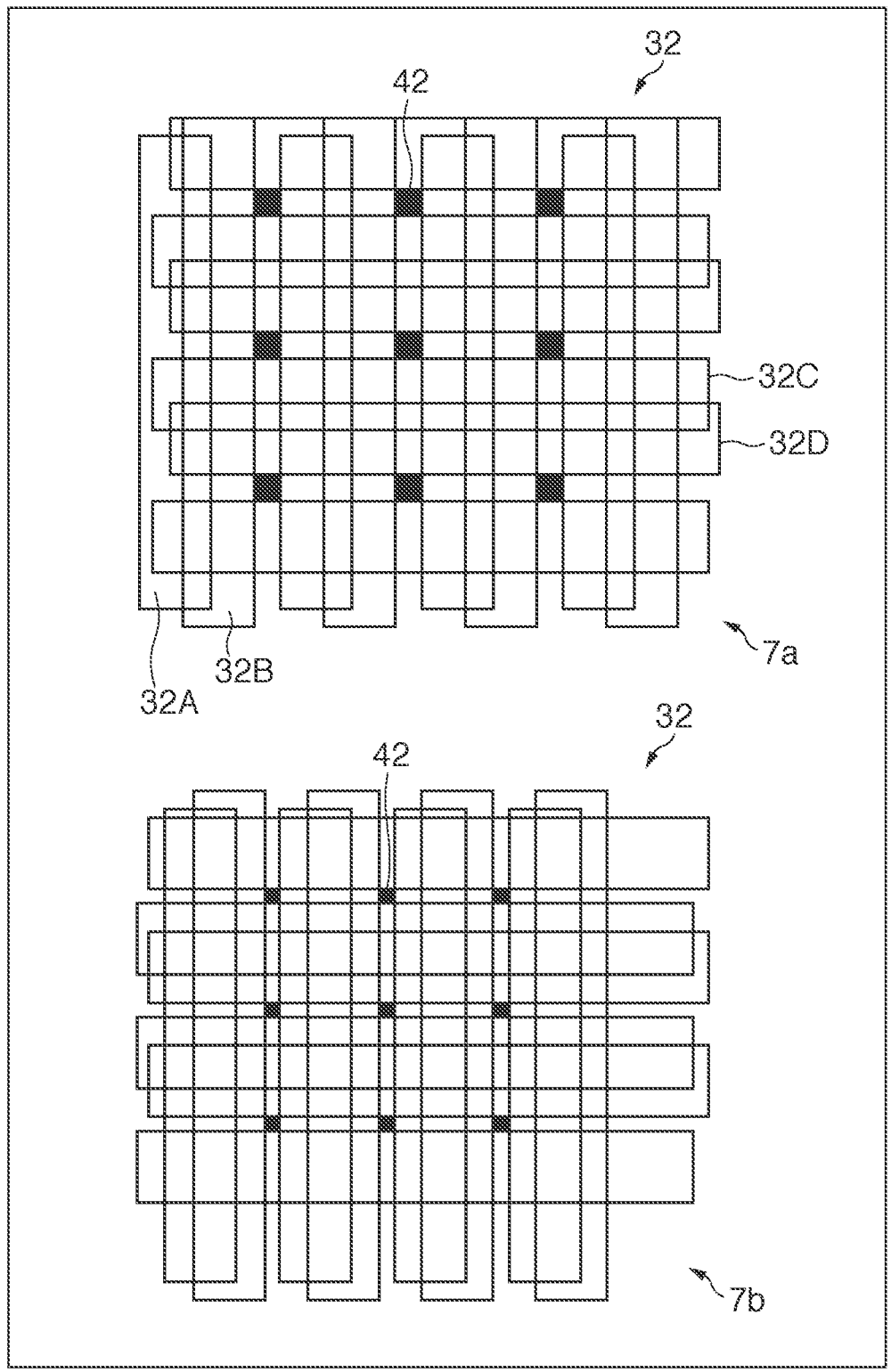
FIG. 7 is a plan view of the stop unit according to the embodiment of the present invention.

The function of the stop unit 27 will be described next with reference to FIG. 6. For the sake of descriptive simplicity, the description made with reference to FIG. 6 is limited to one-dimensional directions. However, since operations in the respective dimensions are independent of each other, it is possible to easily extend one-dimensional operation to two-dimensional operation. 6a in FIG. 6 indicates a case in which the system controls a stop plate 32 to make the respective X-ray sources constituting the multi X-ray source 26 have irradiation regions in the same place on the two-dimensional X-ray detector 28. The stop plate 32 is a member to shield X-rays, and is made of tungsten, lead, copper, iron, or an alloy of them. As shown in FIG. 7, the stop plate 32 can be constituted by four types of stop plates 32A, 32B, 32C, and 32D. The stop unit 27 includes the set of stop plates 32 and a driving unit (not shown) to drive them. Referring to FIG. 6, vacuum partitions 14 are provided between the stop unit 27, the transmission target 13, and the in-vacuum X-ray shield 23.

6b in FIG. 6 indicates a case in which the system performs tomography of the region of interest 33 by using the stop unit 27. The control unit 29 controls the stop plates to make the irradiation regions formed by a transmission target ti and another transmission target tj include the region of interest 33, thereby forming X-ray transmission windows. It is possible to perform X-ray transmission window formation control using the stop plate 32 for only portions (stop apertures 42) corresponding to the selected transmission targets (X-ray focuses). It is however possible to change stop apertures which are not selected for the sake of control. FIG. 7 shows an example of control of the stop plate 32. 7a and 7b in FIG. 7 correspond to 6a and 6b in FIG. 6 and indicate a case in which tomography is performed upon reduction of the irradiation field. It is preferable to complete control of the stop plate 32 to obtain an appropriate size of stop apertures 42 before the start of tomography. This makes it possible to perform high-speed tomography and avoid image deterioration due to the movement of a patient or organ.

As described above, according to the embodiment of the present invention, it is possible to perform tomography at high speed by using the multi X-ray source without simultaneously moving (displacing) the X-ray sources or the two-dimensional X-ray detector.

The present invention is also implemented by executing the following processing. This processing is the processing of supplying software (programs) for implementing the functions of the above embodiment to a system or apparatus via a network or various kinds of storage media, and causing the computer (or the CPU, MPU, or the like) of the system or apparatus to read out and execute the programs.

The present invention is not limited to the above embodiment and various changes and modifications can be made within the spirit and scope of the present invention. Therefore, to apprise the public of the scope of the present invention, the following claims are made.

The invention claimed is:

1. An X-ray imaging apparatus for capturing an X-ray tomogram of an object, comprising:
    a selection unit configured to select two X-ray focuses out of a plurality of X-ray focuses which project images on an X-ray detector through a region of interest which is an imaging region of the object, the selected two X-ray focuses having an intersecting angle of a predetermined value in the region of interest; and
    a control unit configured to control the X-ray focuses existing between the selected two X-ray focuses to emit X-rays and to control the X-ray detector to detect the emitted X-rays, for capturing an X-ray image,
    wherein, after the two X-ray focuses are selected by the selection unit, the selection unit selects other two X-ray focuses by decreasing the intersecting angle in the region of interest.

2. The X-ray imaging apparatus according to claim 1, wherein, when the selected two X-ray focuses are not included in the plurality of X-ray focuses, the selection unit selects the other two X-ray focuses by decreasing the predetermined value of the intersecting angle.

3. The X-ray imaging apparatus according to claim 1, wherein, when the intersecting angle of the selected two X-ray focuses does not match the predetermined value, the selection unit selects the other two X-ray focuses by decreasing the predetermined value of the intersecting angle.

4. The X-ray imaging apparatus according to claim 1, further comprising a display unit configured to perform error display when the two X-ray focuses are not included in the plurality of X-ray focuses,
    wherein, when a positional relationship between an X-ray source and the X-ray detector is changed in accordance with the error display, the selection unit selects the other two X-ray focuses.

5. The X-ray imaging apparatus according to claim 4, wherein contents displayed by the error display include a current value and a desired value of a distance between an X-ray source and the region of interest, and a current value and a desired value of a distance between the X-ray detector and the region of interest.

6. A method of controlling an X-ray imaging apparatus for capturing an X-ray tomogram of an object, the method comprising:
- selecting two X-ray focuses out of a plurality of X-ray focuses which project images on an X-ray detector through a region of interest which is an imaging region of the object, the selected two X-ray focuses having an intersecting angle of a predetermined value in the region of interest; and
- controlling the X-ray focuses existing between the selected two X-ray focuses to emit X-rays and to control the X-ray detector to detect the emitted X-rays, for capturing an X-ray image,
- wherein, after the two X-ray focuses are selected by the selecting, selecting is repeated to select other two X-ray focuses by decreasing the intersecting angle in the region of interest.

7. A non-transitory computer-readable storage medium storing thereon a computer-executable program for causing a computer to control an X-ray imaging apparatus according to a method of controlling the X-ray imaging apparatus for capturing an X-ray tomogram of an object, the method comprising:
- selecting two X-ray focuses out of a plurality of X-ray focuses which project images on an X-ray detector through a region of interest which is an imaging region of the object, the selected two X-ray focuses having an intersecting angle of a predetermined value in the region of interest; and
- controlling the X-ray focuses existing between the selected two X-ray focuses to emit X-rays and to control the X-ray detector to detect the emitted X-rays, for capturing an X-ray image,
- wherein, after the two X-ray focuses are selected by the selecting, selecting is repeated to select other two X-ray focuses by decreasing the intersecting angle in the region of interest.

8. An X-ray imaging apparatus for capturing an X-ray tomogram of an object, comprising:
- a selection unit configured to select at least two X-ray focuses out of a plurality of X-ray focuses which project images on an X-ray detector through a region of interest which is an imaging region of the object, the selected at least two X-ray focuses having an intersecting angle of a predetermined value in the region of interest; and
- a control unit configured to control the selected at least two X-ray focuses to emit X-rays for capturing an X-ray image,
- wherein, after the two X-ray focuses are selected by the selection unit, the selection unit selects other two X-ray focuses by decreasing the intersecting angle in the region of interest.

9. A method of controlling an X-ray imaging apparatus for capturing an X-ray tomogram of an object, the method comprising:
- selecting at least two X-ray focuses out of a plurality of X-ray focuses which project images on an X-ray detector through a region of interest which is an imaging region of the object, the selected at least two X-ray focuses having an intersecting angle of a predetermined value in the region of interest; and
- controlling the selected at least two X-ray focuses to emit X-rays for capturing an X-ray image,
- wherein, after the at least two X-ray focuses are selected by the selecting, selecting is repeated to select other at least two X-ray focuses by decreasing the intersecting angle in the region of interest.

10. A non-transitory computer-readable storage medium storing thereon a computer-executable program for causing a computer to control an X-ray imaging apparatus according to a method of controlling the X-ray imaging apparatus for capturing an X-ray tomogram of an object, the method comprising:
- selecting at least two X-ray focuses out of a plurality of X-ray focuses which project images on an X-ray detector through a region of interest which is an imaging region of the object, the selected at least two X-ray focuses having an intersecting angle of a predetermined value in the region of interest; and
- controlling the selected at least two X-ray focuses to emit X-rays for capturing an X-ray image.

11. An X-ray imaging apparatus for capturing an X-ray tomogram of an object, comprising:
- a selection unit configured to select at least two X-ray focuses out of a plurality of X-ray focuses so that X-rays emitted from the selected X-ray focuses pass through a region of interest of the object; and
- a control unit configured to control the selected at least two X-ray focuses to emit X-rays for capturing an X-ray image of the region of interest,
- wherein the selection unit selects the at least two X-ray focuses out of the plurality of X-ray focuses such that the X-rays emitted from the selected X-ray focuses pass through the region of interest and do not fall outside an X-ray detector.

12. The X-ray imaging apparatus according to claim 11, wherein, when the selected X-ray focuses emit X-rays to intersect each other at the center of the region of interest, the selection unit determines whether or not the emitted X-rays fall outside of the X-ray detector.

13. The X-ray imaging apparatus according to claim 11, wherein the selection unit selects the outermost two X-ray focuses out of the plurality of X-ray focuses, and
- wherein X-rays emitted from the selected outermost two X-ray focuses do not fall outside of the X-ray detector.

14. The X-ray imaging apparatus according to claim 11, wherein the selection unit selects the at least two X-ray focuses such that a region to which X-rays are emitted from the selected X-ray focuses does not become larger than a detection surface of the X-ray detector.

15. A method for controlling an X-ray imaging apparatus for capturing an X-ray tomogram of an object, comprising:
- selecting at least two X-ray focuses out of a plurality of X-ray focuses so that X-rays emitted from the selected X-ray focuses pass through a region of interest of the object; and
- controlling the selected at least two X-ray focuses to emit X-rays for capturing an X-ray image of the region of interest,
- wherein in the selecting, the at least two X-ray focuses are selected out of the plurality of X-ray focuses such that the X-rays emitted from the selected X-ray focuses pass through the region of interest and do not fall outside an X-ray detector.

* * * * *